United States Patent [19]

Pringle

[11] Patent Number: 5,792,087

[45] Date of Patent: Aug. 11, 1998

[54] INJURY PREVENTING ANKLE BRACE

[76] Inventor: Joe Pringle, 381 Tenney Cir., Chapel Hill, N.C. 27514

[21] Appl. No.: 740,494

[22] Filed: Oct. 30, 1996

[51] Int. Cl.[6] ..................................................... A61F 5/00
[52] U.S. Cl. ............................................. 602/27; 602/23
[58] Field of Search ..................................... 602/5, 12, 23, 602/27, 65, 78; 128/882; 36/89, 90

[56] References Cited

U.S. PATENT DOCUMENTS

| | | | |
|---|---|---|---|
| 3,064,644 | 11/1962 | Patterson | 602/23 |
| 3,303,584 | 2/1967 | Werner et al. | 36/120 |
| 4,719,926 | 1/1988 | Nelson . | |
| 4,753,229 | 6/1988 | Sutherland | 602/27 |
| 4,771,768 | 9/1988 | Crispin . | |
| 4,809,686 | 3/1989 | Crane . | |
| 4,922,630 | 5/1990 | Robinson | 36/89 |
| 5,056,509 | 10/1991 | Swearington | 36/89 X |
| 5,069,202 | 12/1991 | Prock . | |
| 5,094,232 | 3/1992 | Harris | 602/27 X |
| 5,209,722 | 5/1993 | Miklaus et al. . | |
| 5,429,588 | 7/1995 | Young | 602/27 |
| 5,454,173 | 10/1995 | Falguere et al. | 36/117.2 |

FOREIGN PATENT DOCUMENTS 2454295  11/1980  France ....................................... 602/16

*Primary Examiner*—Lynne A. Reichard
*Assistant Examiner*—Denise Pothier
*Attorney, Agent, or Firm*—Kennedy Covington Lobdell & Hickman, LLP

[57] ABSTRACT

An ankle brace for limiting and controlling pivotal movement of the foot about the ankle joint of the wearer which includes an upper cuff attachable to the leg of the wearer, a lower support member attachable about the shoe of the wearer, and a pair of longitudinally extending braces arranged to extend downward along on the inside and outside of the ankle of the wearer. Stop members are provided for engaging the brace member and restricting pivotal movement of the foot about the ankle joint to prevent injury-causing excessive inversion or eversion movement of the foot about the ankle joint.

11 Claims, 6 Drawing Sheets

INJURY PREVENTING ANKLE BRACE

BACKGROUND OF THE INVENTION

The present invention related generally to ankle braces, and more particularly to ankle braces of the type designed to restrict certain movements of the foot about the ankle of the wearer.

The ankle joint permits two types of pivotal movement of the talus or ankle bone about the leg bone, namely a generally up and down pivotal movement of the foot within the plane of the leg bone, commonly referred to as dorsiflexion and plantarflexion, and side-to-side pivotal movement of the foot relative to the ankle, commonly referred to as inversion and eversion. The complexity of motion between foot and leg that is permitted by the ankle is necessary to allow the kind of function that permits athletic activity. As is well known, excessive inversion of the foot can damage the ligaments at the ankle joint and cause ankle sprain which is a painful and sometimes debilitating injury.

One commonly used technique for reducing the possibility of ankle sprain, or for reducing the possibility of reinjury, is to wrap tape tightly around the ankle joint to partially restrict pivotal movement of the foot about the leg, but such tape is not always capable of restricting or preventing excessive inversion of the foot that may cause ankle sprain, particularly after it become wet with perspiration, and it can be time consuming to apply the tape at frequent intervals, as well as uncomfortable and irritating to the wearer.

Accordingly, a wide variety of mechanical or orthopedic appliances have been designed to protect the foot against undesirable movement during rehabilitation. These braces are generally quite bulky and permit only limited movement of the foot and, when wearing such a brace, the user can only engage in limited physical activities. Typical examples of braces of this type are disclosed in Crispin U.S. Pat. No. 4,771,768 and Young U.S. Pat. No. 5,429,588.

Additionally, ankle braces have been designed primarily to prevent injury or reinjury of the ankle joint by restricting movement of the foot about the leg at the ankle joint while generally permitting a greater range of movement than the more restrictive rehabilitation braces so that the wearer can still participate in athletics. These ankle braces are sometimes designed to be used inside the shoe of the wearer, such as the braces disclosed in Harris U.S. Pat. No. 5,094,232 and Miklaus U.S. Pat. No. 5,209,722, while others are designed for use outside of the shoe, such as the brace disclosed in Crane U.S. Pat. No. 4,809,686.

Ankle braces designed for use inside the shoe of the wearer have several drawbacks. Most importantly, braces worn within the shoe are located closer to the foot than those worn outside of the shoe, and, as a result, forces acting on the shoe, if it is worn during athletic events, have a greater mechanical advantage in terms of transmitting those forces to the components of the brace designed to withstand such forces. Therefore, braces of this type must be either too bulky, heavy, and/or restrictive to be suitable for athletic activities, or they are not sturdy enough to withstand the large forces that act upon the components of the brace. Finally, since these braces must be worn tightly, and since athletic shoes are not designed to accommodate braces within the confines of the shoe, they can be very uncomfortable for the wearer, particularly during strenuous athletic activities such as basketball.

More importantly, in most known ankle braces, whether of the inside-the-shoe or outside-the-shoe type, the range of movement permitted by the brace is essentially limited to plantarflexion and dorsiflexion, with only minimal or nonexistent inversion and eversion movement, and, while limiting movement to this extent may be desirable in many applications of an ankle brace (e.g., rehabilitation from ankle injury), it renders the brace useless when worn by someone engaged in athletic activities. This is because some inversion/eversion movement is necessary when planting a foot to change directions or maintaining balance on uneven ground. In some known braces, limited inversion or eversion movement may be permitted, but it is not controlled in any way, and/or the brace itself involves a complicated, heavy construction that makes it undesirable. For example, in the aforesaid Crane U.S. Pat. No. 4,809,686, some inversion/eversion movement appears to be permitted by simply making somewhat loose connections at the respective ends of the downwardly extending brace member, but there is no mechanism for precisely controlling such movement to an extent that would freely allow a full range of inversion/eversion movement while also preventing excessive inversion of the ankle. In Harris U.S. Pat. No. 5,094,232, a very complicated mechanism is provided for defining the range of movement of the foot of the wearer which includes a pair of facing plates having cooperating indentations or grooves formed in the plates with a ball bearing pivot captured between the plates, and a Belleville spring for holding the plates together. While this complicated mechanism does allow a range of movement of the foot about the leg, it is intended to be worn within the shoe with all of the inherent disadvantages discussed above being exacerbated by the size and complexity of the brace which must be contained within the shoe of the wearer, and the nature of the mechanism, with its slots, ball bearing pivots, and springs would appear to make it susceptible to mechanical failure as a result the constant and substantial forces to which it is exposed if the brace is worn during strenuous athletic events, such as basketball.

Accordingly, there is a need for a simple, inexpensive ankle brace that can be comfortably worn and that freely permits a normal range of movement of the foot at the ankle joint while simultaneously preventing excessive movement that might cause injury or reinjury to the wearer.

SUMMARY OF THE INVENTION

The present invention comprises an ankle brace for permitting normal pivotal movement of the foot about the ankle of the wearer, both dorsiflexion/plantarflexion and inversion/eversion, while preventing injury causing excessive inversion movement of the ankle, and it includes an upper cuff member selectively attachable about the leg of the wearer at a predetermined location on the leg, a lower support member selectively attachable about the outside of the shoe of the wearer, at least one generally rigid and longitudinally extending brace member attached to the upper cuff member and extending downwardly therefrom along and adjacent the ankle of the wearer, and an attachment assembly means connecting the lower end of the brace member to the lower support member. The lower support member may be removably attached to the shoe by straps or permanently attached to the shoe itself.

In one embodiment of the present invention, the attachment assembly includes a slot formed in the brace member and extending in the direction of the longitudinal extent of the brace member to permit vertical travel of this member, and a pin element formed in the lower support member, with the pin element extending through the slot and having a predetermined extending length substantially greater than the thickness of the slot to permit a predetermined amount of relative movement of the brace member away from the lower brace member. A stop member is positioned to engage the brace member during the downward movement thereof when the inversion pivoting movement of the foot of the wearer reaches a predetermined limit.

In another embodiment of the present invention, the longitudinally extending brace member extends downwardly into a somewhat rigid pocket on the lower brace member. The pocket is dimensioned so that it permits not only sliding movement of the longitudinally extending brace member therethrough, but it also permits a predetermined amount of relative lateral movement of the brace member away from the lower support member. Additionally, this embodiment may have a window in the pocket through which a projection attached to the longitudinally extending brace member protrudes to limit its movement and prevent the longitudinally extending brace member from slipping out of the pocket.

Preferably, the stop is in the form of a pocket located at a predetermined location below the lower end of the brace member in its normal position, with the lower end of the brace member entering the pocket during downward movement of the brace member and preventing further movement when the inversion movement of the foot has reached a predetermined limit. Also, the cuff member is preferably worn between the top of the shoe of the wearer and thickest part of the calf of the wearer so that forces transmitted to the cuff through the brace member can be readily absorbed by the cuff member. Finally, it is preferred that the ankle brace of the present invention be provided with two brace members extending downwardly along both sides of the ankle.

DETAILED DESCRIPTION OF THE PREFERRED EMBODIMENT

Looking now in greater detail at the accompanying drawings, FIGS. 1–4 illustrate one embodiment of the ankle brace of the present invention, which includes an upper cuff member 10 that is selectively attachable about the leg of the wearer at a location between the thickest part of the calf and the top of the shoe 12 worn by the wearer. The upper cuff member 10 preferably includes a conventional Velcro connection (not shown) so that it can be easily attached and detached about the leg of the wearer.

A lower support member 14 is selectively attached about the outside of the shoe 12 by a plurality of connecting straps 16, whereby the lower support member 14 is securely held in place at the outside surface of the shoe 12.

Figure 1:
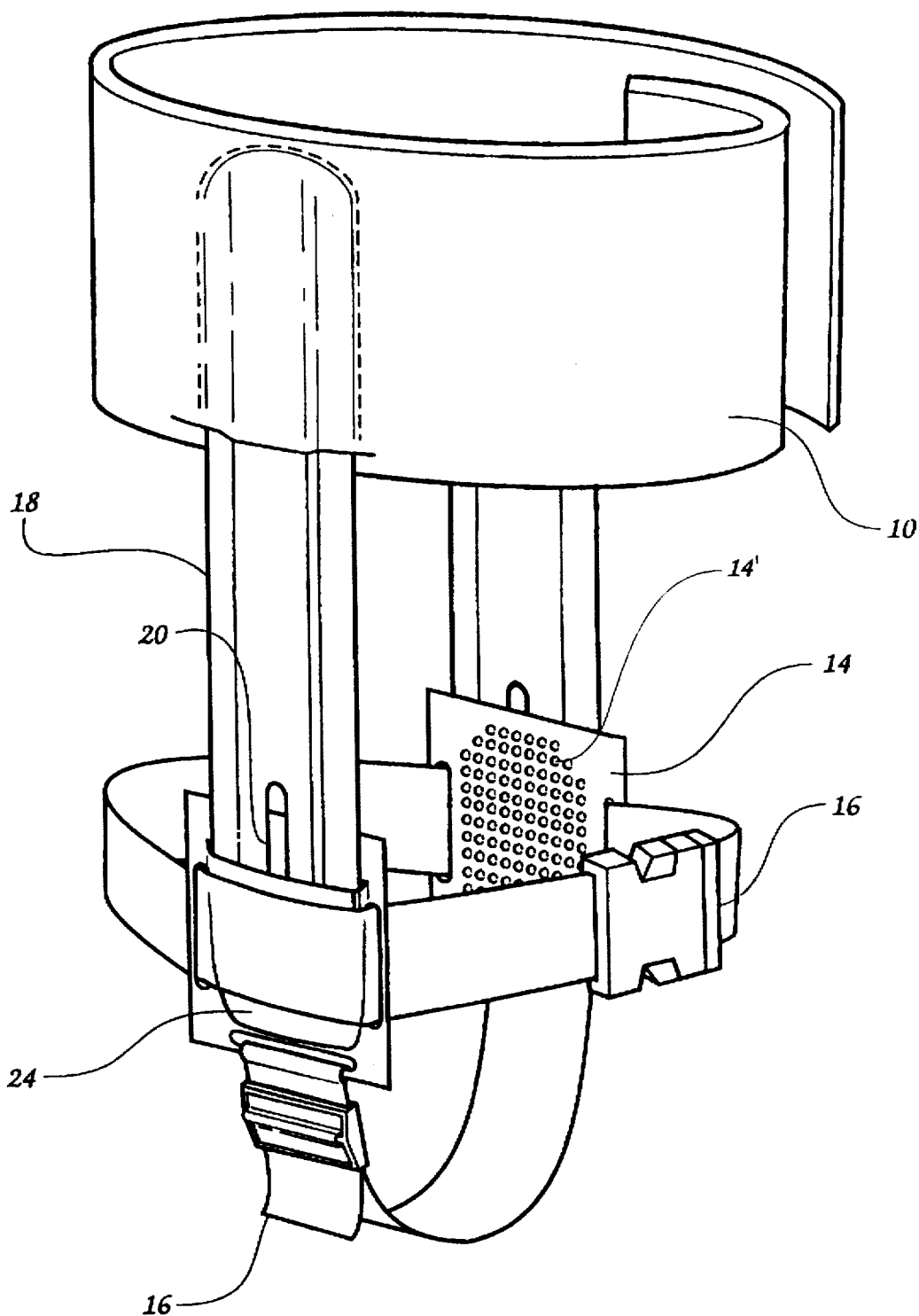
FIG. 1 is a perspective view of one embodiment of the ankle brace of the present invention.
Figure 2:
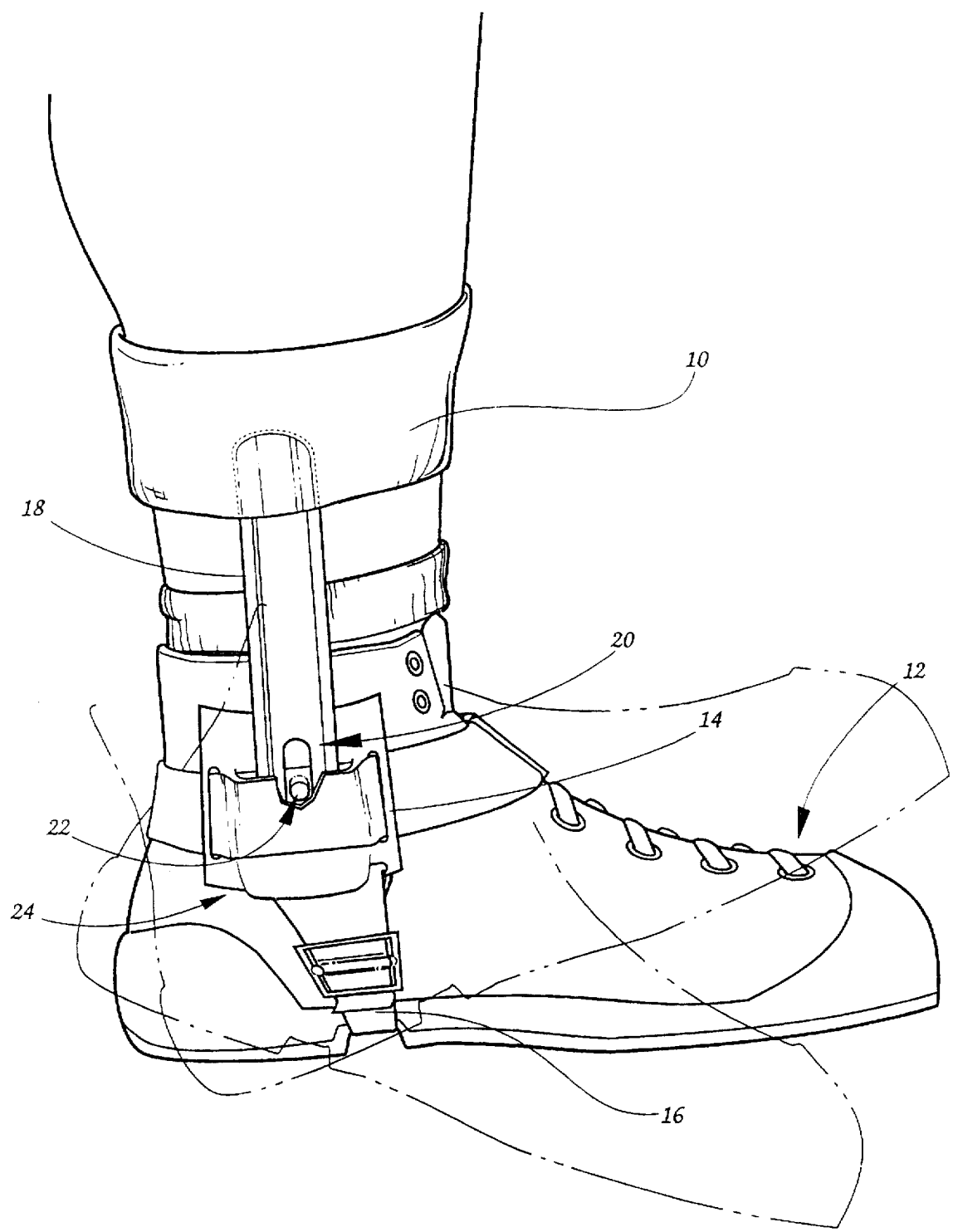
FIG. 2 is a side elevational view of the ankle brace illustrated in FIG. 1 mounted on the leg of a wearer and showing the plantarflexion and dorsiflexion movement of the foot permitted by the ankle brace.
Figure 3:
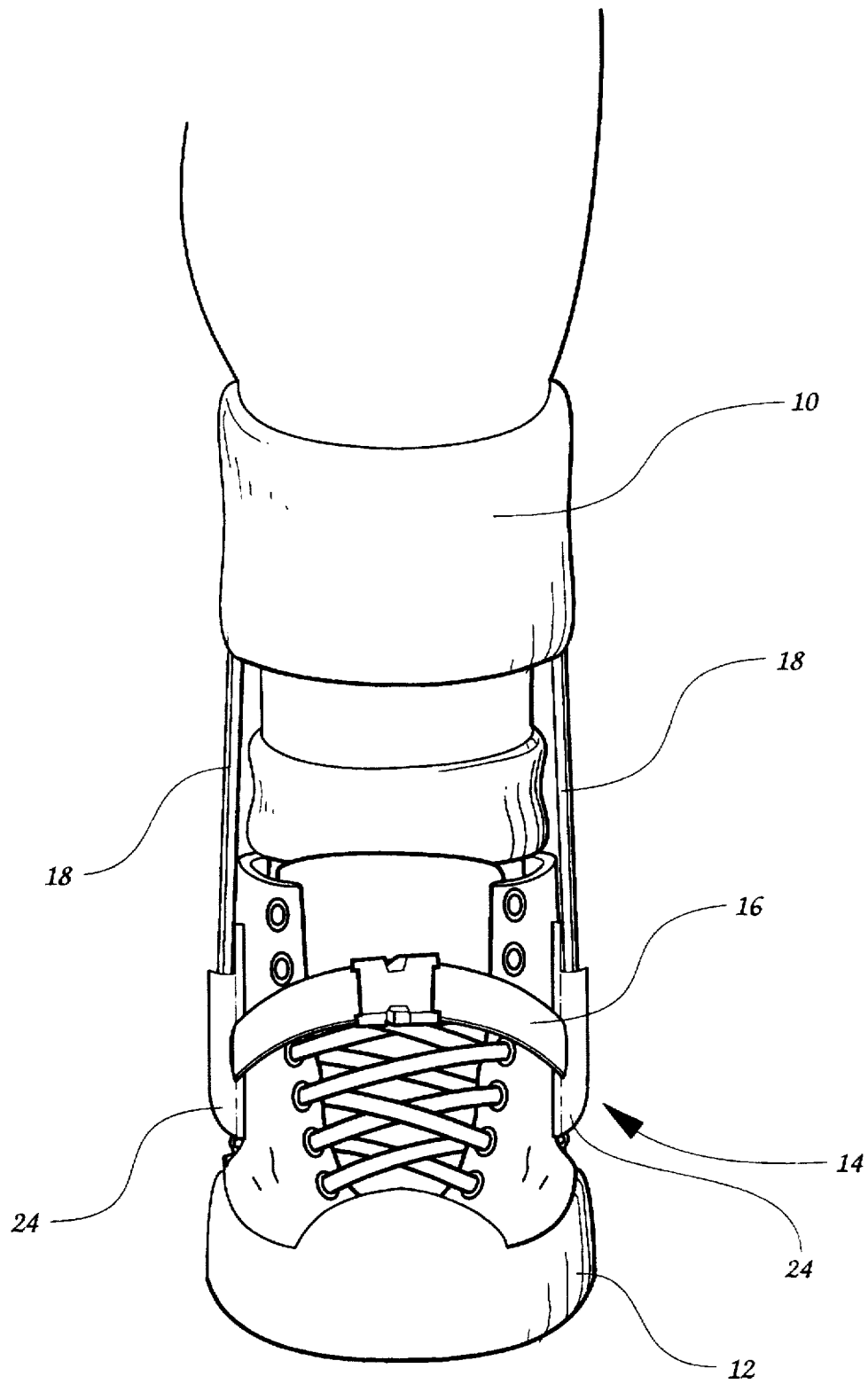
FIG. 3 is a front elevational view of the ankle brace illustrated in FIG. 2.
Figure 4:
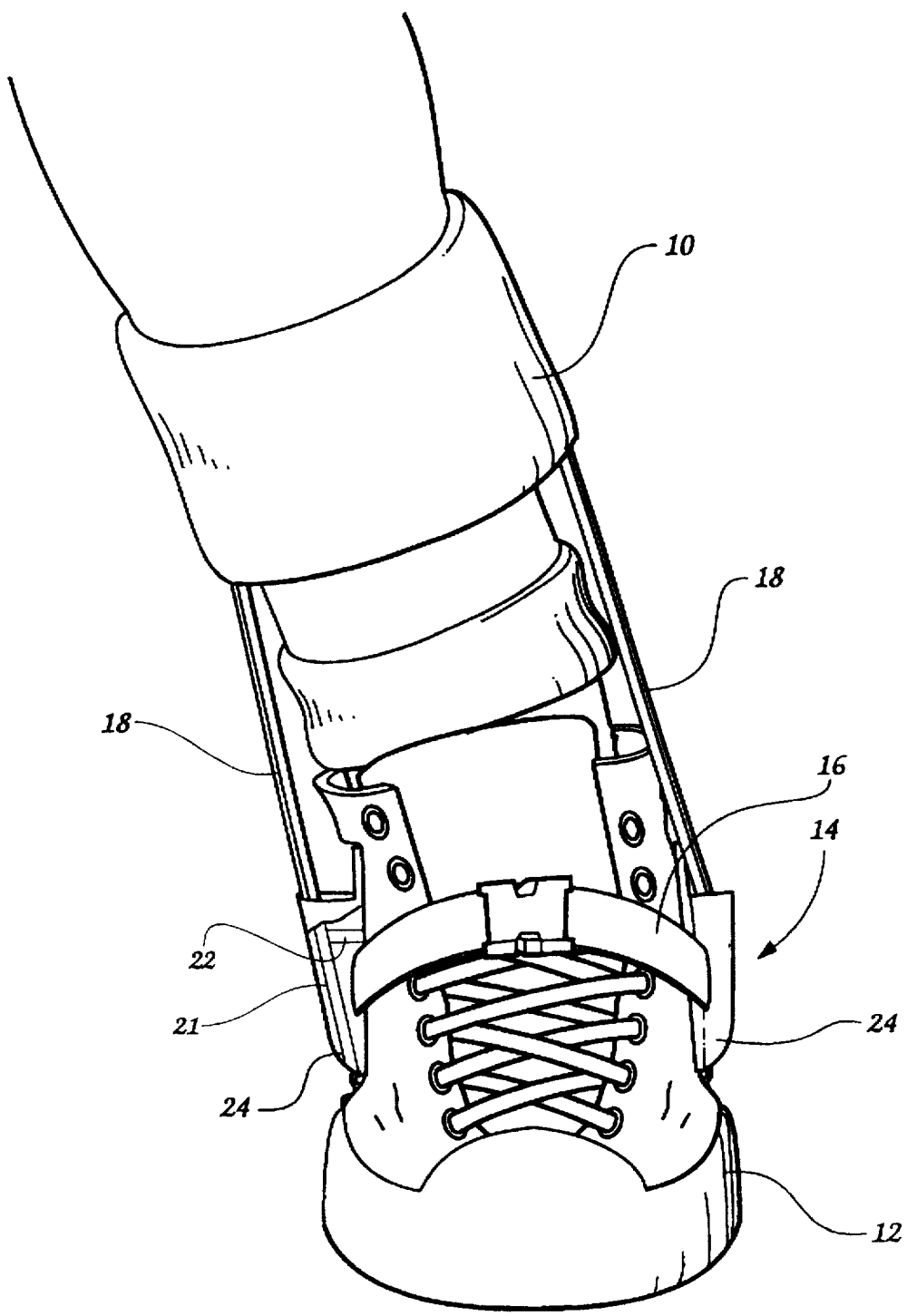
FIG. 4 is a front elevational view similar to FIG. 3, but showing the inversion movement of the foot permitted by the ankle brace.

A pair of generally rigid and longitudinally extending brace members 18 are secured to the upper cuff member 10, and they extend downwardly therefrom along and generally adjacent the inside and outside portions of the ankle of the wearer, as best seen in FIGS. 2 and 3. The braces 18 are identical, and each includes a slot 20 that extends along the longitudinal length of the brace 18 adjacent the lower extending end thereof. The lower support member 14 is provided with a pair of pins 22 that extend outwardly through the slots 20, respectively, and the pins 22 have an extending length that is substantially greater than the thickness of the portions of the brace members 14 adjacent the slots 20 to permit selective movement of the braces 18, as illustrated in FIG. 4 and as will be described in greater detail presently.

The lower support member 14 is also provided with a pair of identical pockets 24 that have a closed lower end and an open upper end that is positioned adjacent the lower end of the braces 18, respectively, and the pins 22 preferably extend to the inside surfaces of the pockets 24. The inside surface of the lower support member 14 may be formed with a pattern of small spikes or protrusions 14' (see FIG. 1) that will engage the material of the shoe 12 and prevent slippage of the lower support member 14 relative to the shoe 12.

The ankle brace, as described above, is designed to be used by persons engaged in generally strenuous exercise, such as playing basketball, and it can be used generally to prevent sprained ankles, or it can be used by a person in the process of recovering from a previous ankle sprain so as to prevent a recurrence of the sprain.

As best seen in FIGS. 2 and 3, the ankle brace permits normal movement of the foot about the ankle joint. More specifically, as best seen in FIG. 2, dorsiflexion and plantarflexion movement are permitted by virtue of the pivoting movement of the lower support member about the pins 22 extending through the slots 20. Moreover, as best seen in FIG. 3, normal inversion and eversion movement of the foot of the wearer is permitted by virtue of the pins 22 sliding vertically within the slots 20 and by virtue of the fact that the extending length of the pins 22 relative to the thickness of the braces 18 permits some lateral movement of the braces 18 relative to the pins 22. Thus, the ankle brace is specifically designed so that, when it is worn by a person engaged in athletic activities, the attachment assembly consisting of the pins 22 and slots 20 permit movement of the braces 18 in such a way that normal movement of the foot about the ankle joint of the wearer is not inhibited in any way. Moreover, because all of the elements of the ankle brace are located outside of the shoe, the components thereof, particularly the braces 18, can be made of sturdy material so that they are rigid enough to effectively resist inversion at a precise point. This is in contrast to some of the aforesaid known devices which are designed to be located within the confines of the shoe and which require some bending of the components in carrying out these intended functions.

However, as best seen in FIG. 4, the pockets 24 are positioned relative to the braces 18 so that excessive, injury-causing pivotal movement of the foot about the ankle joint is prohibited. More specifically, inversion or eversion movement of the foot about the ankle joint will result in one of the braces 18 sliding into the adjacent pocket 24, and the pockets 24 are designed so that the lower end of the adjacent brace 18 will engage the bottom of the pocket 24 and thereby stop further downward movement of the brace 18, which, in turn, stops further inversion or eversion pivoting movement of the foot of the wearer. By appropriately locating the pockets 24 relative to the braces 18, it will be apparent that the ankle brace will stop pivotal movement of the foot about the ankle joint just before it reaches a predetermined limit that would otherwise result in excessive pivotal movement that could create a severe ankle sprain.

Figure 5:
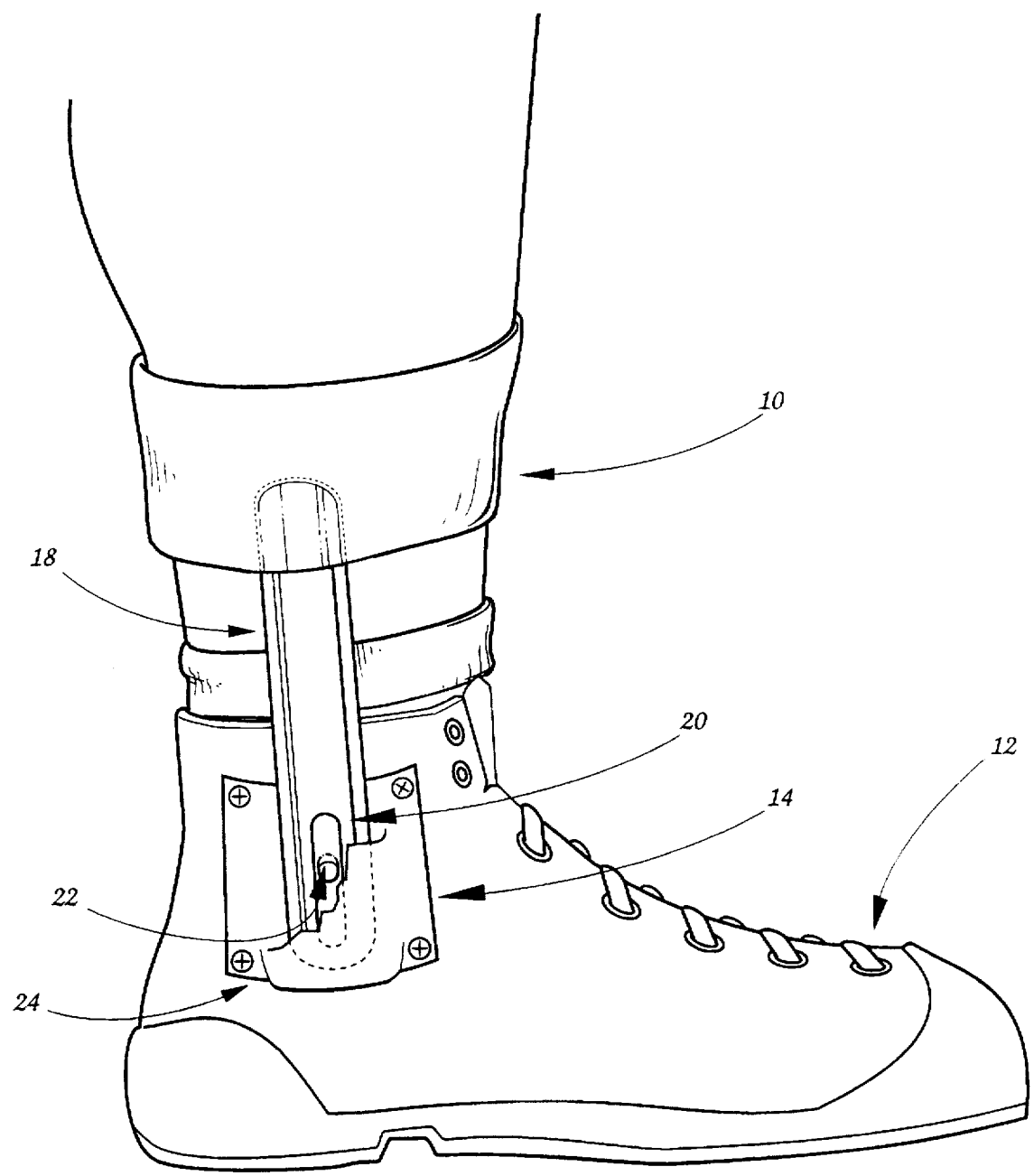
FIG. 5 is a side elevational view of an alternate embodiment of the ankle brace of the present invention.

As best seen in FIG. 5, the lower support member 14 may be permanently affixed to the sides of the shoe 12 using rivets 26 or any other suitable attachment elements. The ankle brace in this embodiment operates in the same manner as that described above in connection with the embodiment illustrated in FIGS. 1–4.

Accordingly, in a typical example, if a person wearing the ankle brace is playing basketball and makes a sudden change in direction which results in one foot being planted to the floor with excessive pivotal movement of the ankle about the planted foot, the ankle brace will not permit the foot to pivot beyond a predetermined limit relative to the leg of the wearer and will thereby prevent injury to the wearer. Moreover, it is significant to note that the forces imposed on the braces 18 during such pivotal movement of the foot will be transmitted directly to the calf of the wearer through the braces 18 and the upper cuff member 10. Looking at FIG. 4, it will be noted that, when the inward or left-hand brace 18 engages the bottom of the pocket 24 during inversion movement of the foot, any further inversion-type forces imposed on the foot will be transmitted upwardly through the brace 18 to the cuff member 10 where such forces can be easily absorbed because the cuff member 10 is preferably located beneath the largest portion of the calf of the wearer. It will also be noted that this upwardly directed force on the cuff member will be offset by the opposite downwardly directed force imposed on the cuff member 10 by the other brace 18 located on the outside of the ankle of the wearer.

Finally, the slots 20 are dimensioned to have an extending length that will result in the pin element 22 abutting the lower end of its adjacent slot at about the same time when the lower end of the other brace 18 hits the bottom of its adjacent pocket 24. Thus, again looking at FIG. 4, when the lower end of the inwardly located brace 18 engages the bottom of its adjacent pocket 24, the pin 22 for the outside brace 18 will abut the lower end of its slot 20 so that no further movement of the pin 22 within the slot 20 is permitted, all of which augments the ability of the ankle brace to prevent pivotal movement of the foot of the wearer beyond a predetermined limit.

Figure 6:
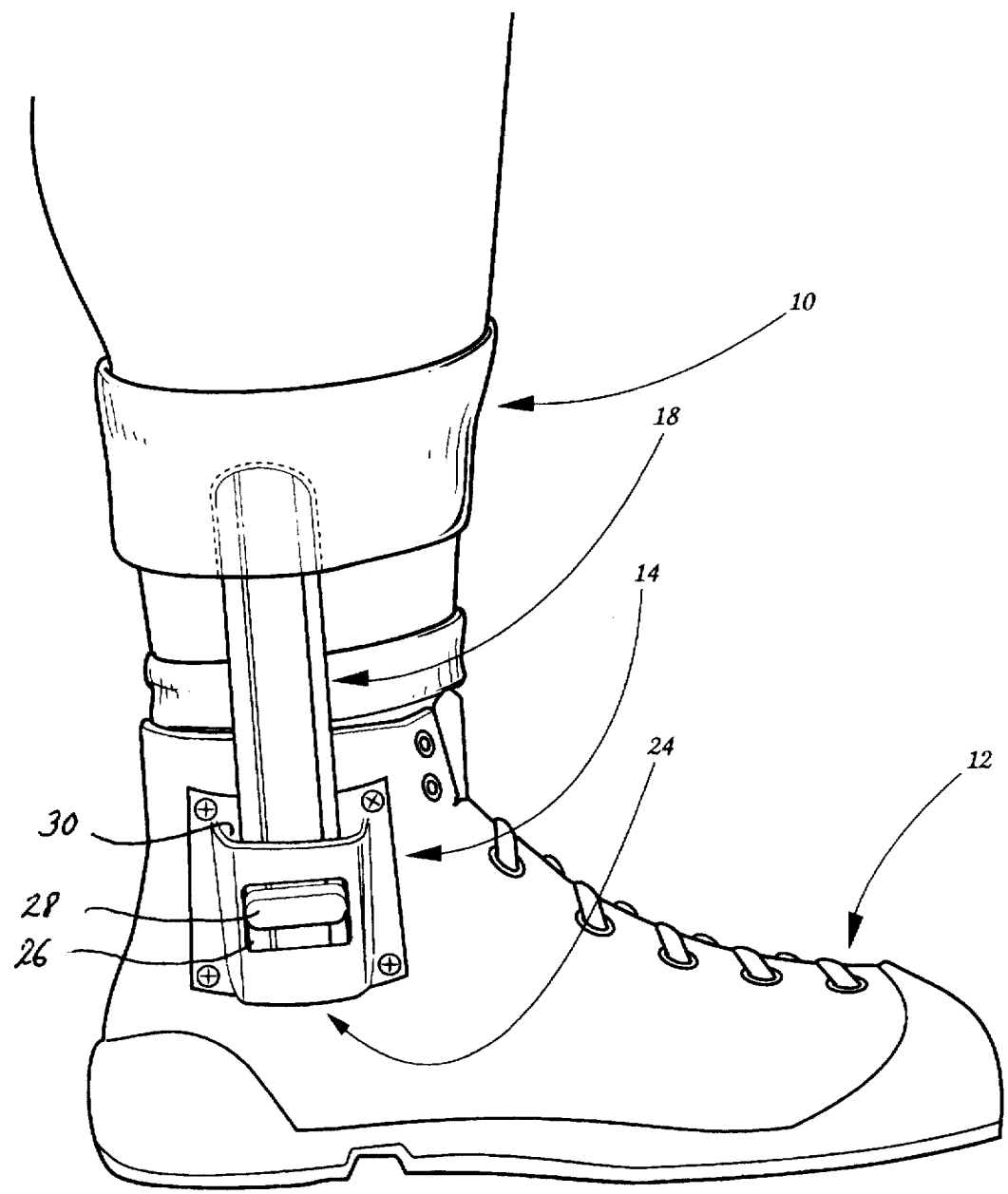
FIG. 6 is a side elevational view of another embodiment of the ankle brace of the present invention.

Another embodiment of the present invention is illustrated in FIG. 6, and it includes an upper cuff member 10 having two braces 18 extending downwardly therefrom and a lower support member 14 secured to the outside of the shoe 12 by straps 16, all in identical manner to that described above. However, in this embodiment of the present invention, the pin and slot attachment assembly in the braces 18 is eliminated, and, instead, each of the pockets 24 is formed with an opening 26, and a projection 28 is fixed to each of the braces 18 so as to protrude outwardly through the openings 26, respectively. The vertical side edges of the projection 28 preferably have a somewhat rounded configuration so that they will have live contact with adjacent sides of the openings 26 that will not inhibit normal dorsiflexion and plantarflexion movement of the foot. In this embodiment, the pocket 24 is preferably made of a somewhat rigid fabric, and the pocket 24 is dimensioned so that it forms with the side of the shoe a slot 30 that permits not only sliding movement of the braces 18 therein, but also permits a predetermined amount of relative lateral movement of the brace member 18 away from the lower support member 14. Additionally, each opening 26 is dimensioned so that the projection 28 will contact with the bottom of the opening 26 when the end of the brace 18 contacts the bottom of the pocket 24 to assist in preventing further inversion of the foot. Also, each projection 28 preferably has a projecting length that is sufficient to prevent the brace member 18 from slipping out of its pocket 24.

The embodiment of the ankle brace illustrated in FIG. 6 operates in substantially the same way as the ankle brace in FIGS. 1–5 in that the braces 18 can float freely within the pockets 24 to permit all of the normal pivotal motions of the foot about the ankle joint as described above. If, however, the pivotal movement of the ankle of the wearer reaches a predetermined limit beyond which injury may occur, the lower end of one of the braces 18 will engage the bottom of its adjacent pocket 24 in the same manner as that described above and will thereby prevent injury causing pivotal movement of the ankle. In view of the simplicity of the design in this embodiment of the present invention, it may be possible, in some instances, to simply incorporate the components of the brace within a specially built shoe, rather than producing the ankle brace as a separate device.

It will be apparent from the above that the ankle brace of the present invention provides a simple, inexpensive ankle brace that can be easily attached to the outside of a shoe of the wearer, with all of the inherent advantages of an outside brace described above. Moreover, this simple and inexpensive ankle brace readily permits normal movement of the ankle about the foot in all directions, while at the same time carefully controlling or limiting pivotal movement of the ankle beyond a predetermined limit to thereby ensure that the user of the ankle brace will not incur a debilitating ankle injury or will not reinjure an ankle recovering from a prior ankle sprain.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An ankle brace for permitting normal pivotal movement of the foot about the ankle joint of the wearer while preventing injury-causing excessive inversion or eversion movement of the foot about the ankle joint, said ankle brace comprising:

(a) an upper cuff member selectively attachable about the leg of the wearer at a predetermined location on the leg;

(b) a lower support member selectively attachable to the shoe of the wearer;

(c) at least one generally rigid and longitudinally extending brace member attached to said upper cuff member and extending downwardly therefrom along and adjacent the ankle of the wearer;

(d) an attachment assembly means connecting a lower end of said brace member to said lower support member which includes slot means formed in one of said brace member or said lower support member that permits sliding movement of said brace member relative to said lower support member and that permits a predetermined amount of relative lateral movement of said brace member away from said lower support member whereby a controlled amount of inversion or eversion movement of the foot about the ankle is permitted; and (e) a stop member positioned to engage said brace member during said downward movement thereof when the inversion movement of the foot of the wearer reaches a predetermined limit.

2. An ankle brace as defined in claim 1, wherein said slot means includes a slot formed in said brace member extending in the direction of the longitudinal extent thereof, and a pin element mounted on said lower support member, said pin element extending through said slot and having a predetermined length substantially greater than the thickness of said brace member.

3. An ankle brace as defined in claim 2, wherein said stop member comprised the upper end of said slot to prevent further downward movement of said brace member when said pin abuts said upper end of said slot.

4. An ankle brace as defined in claim 2, wherein said pin element has an effective extending length substantially greater than the thickness of said brace member adjacent said slot such that said brace member can slide laterally along the effective extending length of said pin to permit said lateral movement of said brace member outwardly from the lower support member.

5. An ankle brace as defined in claim 1, wherein said stop member includes a pocket attached to said lower support member and positioned to receive the lower end of said brace member and stop further downward movement thereof.

6. An ankle brace as defined in claim 1, wherein said attachment assembly means connects said lower end of said brace member to said lower support member and further includes a pocket spaced from the side of the shoe, and wherein the bottom of said pocket is attached to the shoe to form said stop member.

7. An ankle brace as defined in claim 6, wherein said pocket is dimensioned to permit said lateral movement of said brace member outwardly from the lower support member.

8. An ankle brace as defined in claim 1, wherein said upper cuff member is attachable to the leg between the top of the shoe of the wearer and the thickest portion of the calf of the wearer.

9. An ankle brace as defined in claim 1, wherein said lower support member includes connecting straps for extending around the shoe of the wearer to secure said lower support member to the outside of said shoe.

10. An ankle brace as defined in claim 1, wherein a second generally rigid and longitudinally extending brace member is attached to said upper cuff member and extends downwardly therefrom along and adjacent the other side of the ankle of the wearer, said second brace member being attached to said lower support member by a second attachment assembly means which includes a second pin element attached to said lower support member and extending through a second slot formed in said second brace member.

11. An ankle brace for permitting normal pivotal movement of the foot about the ankle joint of the wearer while preventing injury causing excessive inversion or eversion movement of the foot about the ankle joint, said ankle brace comprising:

(a) a lower support member having connecting straps for removably attaching said lower support member about the outside of the shoe of the wearer;

(b) an upper cuff member selectively attachable about the leg of the wearer at a predetermined location on the leg of the wearer between the top of the shoe and the thickest part of the calf of the wearer;

(c) a pair of generally rigid and longitudinally extending brace members attached to said upper cuff member and extending downwardly therefrom along and generally adjacent the inside and outside portions of the ankle of the wearer;

(d) an attachment assembly means connecting a lower end of said brace members to said lower support member which includes a slot formed adjacent the downwardly extending end of each brace member and a pair of pin elements attached to said lower support member and extending through said slots in said brace members, respectively, said pins having an extending length that is substantially greater than the thickness of the portions of said brace members adjacent said slots to permit:

(i) pivotal movement of the lower support member about said brace members;

(ii) sliding movement of said brace members relative to said lower support member in the direction of said longitudinal extent of said brace members; and (iii) lateral movement of said brace members outwardly and inwardly from said lower support member; and (e) a pocket formed on said lower support member and positioned to receive a lower end of one of said brace member and stop further downward movement thereof when the inversion movement of the foot of the wearer reaches a predetermined limit.

* * * * *